(12) United States Patent
Sevillano Delgado

(10) Patent No.: US 9,744,018 B2
(45) Date of Patent: Aug. 29, 2017

(54) TENSOR PULLEY FOR GLUTEUS

(71) Applicant: Manuel Sevillano Delgado, Bogota (CO)

(72) Inventor: Manuel Sevillano Delgado, Bogota (CO)

(*) Notice: Subject to any disclaimer, the term of this patent is extended or adjusted under 35 U.S.C. 154(b) by 353 days.

(21) Appl. No.: 14/506,255

(22) Filed: Oct. 3, 2014

(65) Prior Publication Data
US 2015/0265389 A1 Sep. 24, 2015

(51) Int. Cl.
| | | |
|---|---|---|
| *A61F 2/00* | (2006.01) | |
| *A61B 17/04* | (2006.01) | |
| *A61B 17/00* | (2006.01) | |
| *A61B 17/06* | (2006.01) | |

(52) U.S. Cl.
CPC ........ *A61F 2/0059* (2013.01); *A61B 17/0401* (2013.01); *A61B 2017/00792* (2013.01); *A61B 2017/00796* (2013.01); *A61B 2017/0427* (2013.01); *A61B 2017/0464* (2013.01); *A61B 2017/06176* (2013.01)

(58) Field of Classification Search
CPC .... A61K 39/39558; A61B 2018/00505; A61B 2018/00517; A61B 2018/00523
See application file for complete search history.

(56) References Cited

U.S. PATENT DOCUMENTS

| | | | | |
|---|---|---|---|---|
| 2006/0198869 A1* | 9/2006 | Furst | ......................... | A61F 2/91 424/426 |
| 2007/0156175 A1* | 7/2007 | Weadock | ........... | A61B 17/0401 606/216 |
| 2008/0009936 A1* | 1/2008 | Kim | ....................... | A61B 17/11 623/1.15 |
| 2012/0158155 A1* | 6/2012 | Shin | .......................... | A61F 2/04 623/23.66 |

\* cited by examiner

*Primary Examiner* — Christine H Matthews
*Assistant Examiner* — Joshua D Lannu
(74) *Attorney, Agent, or Firm* — Porzio Bromber & Newman P.C.

(57) ABSTRACT

A device for carrying out Gluteopexia, which is the elevation of the buttocks. The device has longitudinal shape and is composed by a first anchoring element and a second anchoring element, both linked by a longitudinal element, combining for a single body. The first anchoring element is sheltered in a longitudinal crevice of the first cover of the device. The second anchoring element is lodged in a longitudinal channeled piercing of the second cover of the device.

11 Claims, 8 Drawing Sheets

TENSOR PULLEY FOR GLUTEUS

BACKGROUND OF THE INVENTION

Field of the Invention

This invention applies to the technical field of the surgical devices and methods that are minimally invasive, particularly to a device to perform Gluteopexia (elevation of the gluteus).

Description of Related Art

The Greek term Ptosis means falling and in medicine this term defines a condition of tissue or an organ of the body, where such tissue or organ has fallen or is lagging with respect to its previous position. The technical field concerning this invention relates more specifically to Ptosis Glutea, meaning the falling of the gluteus due to the increase of its volume and flaccidness.

Since Ptosis Glútea is not considered a medical condition but a case of corporal esthetics, it can be corrected by means of esthetic surgery. The type of intervention performed to raise and project the gluteus is called Gluteopexy. Many techniques have been developed in the field of aesthetic surgery aimed at bettering the appearance of the gluteus so that they fit into the general parameters of beauty and harmony. These techniques range from the augmentation of the gluteus through the use of a prosthesis, to the use of flaps and also include using suspension threads for the skin. Nevertheless, in the current state of plastic and aesthetic medicine, the techniques that have been used have not managed to produce a real outcome in the lifting of fallen gluteus.

Some methods and devices to treat mammary ptosis are revealed in the documents containing patents US2013066423A1 and WO2010051506A1, by means of fixing suspension threads on the tissues of the body.

Document US2013066423A1 refers to the means of using an apparatus and the methods to elevate the tissues, to correct a ptosis condition caused by the stretching of the tissue. In some of the techniques, the tissue is supported by a support member and tension is applied on the support member through at least one suspension member. The procedures described in the above invention provide examples of methods and apparatus to be used in the lifting or to apply tension on various tissues, including: tissues in the breasts, thighs, arms, abdomen, neck and face.

This publication describes a technique for the raising of the tissue using a means of support which can be manufactured out of lactic acid bio-copolymers (see paragraph [0117] page 6).

In the same manner, we make reference to FIGS. 29a: 29B; 32a and 32b containing the American invention where the different supports to be used are shown.

Document WO2010051506A1 refers to the methods and devices to be used to support the tissues in the body of the patient. In some techniques, this invention is applied on the mammary tissue or on any other tissue. A system for tissue support is described, in which an elongated element can be included; a flexible sling (3712) that has a first end and a second end and is configured to be introduced subcutaneously by using a generally half-lateral axis, a first line of suspension (3735) that goes from the first anchor in the soft tissue (3734) and has a free topmost end, and a second line of suspension (3735) that is attached to a second lower anchor for soft tissue (3734) and has a second topmost free end, the first topmost free end can be arranged to be connected to the first end of the sling (3712), and the second topmost free end can be configured to be connected to the second end of the sling (3712).

This publication describes a technique for the raising of the tissue using a means of support or anchor that is connected to give support to the tissue that is to be lifted. It can also be applied to the tissue in the gluteus (see paragraphs [0017]; [0024]; [0027]; [0033]; [0041]; [0243]; [0314]; [0449]; and [0577]).

SUMMARY OF THE INVENTION

According to this invention, we are given a technique based on the mechanical principle of pulleys, which guarantees attaining the raising effect of the gluteus and sustain it indefinitely.

This invention describes a device that features anchor elements that have been developed to be fixed in a secure and practical way on the crest of the iliac bone and not on the soft tissues of the body, which makes this surgical procedure very efficient and long lasting in keeping the gluteus in their new position. On the other hand, this invention also makes improvement on existing techniques by developing a device that has sheaths that cover the anchoring elements and have been designed to be removed easily, and also to be absorbed in a mid-term range. This procedure is carried out in a quick, easy and secure manner using this anchoring element in the surgery.

According to this invention, a device which provides a means to separate the weight of the gluteus in two support forces is provided. These forces are supported on two anchor points in the body of the person to be treated. Where the first support point is the anterior-superior iliac spine and the second is the lumbosacral ligaments.

DETAILED DESCRIPTION

Figure 1:
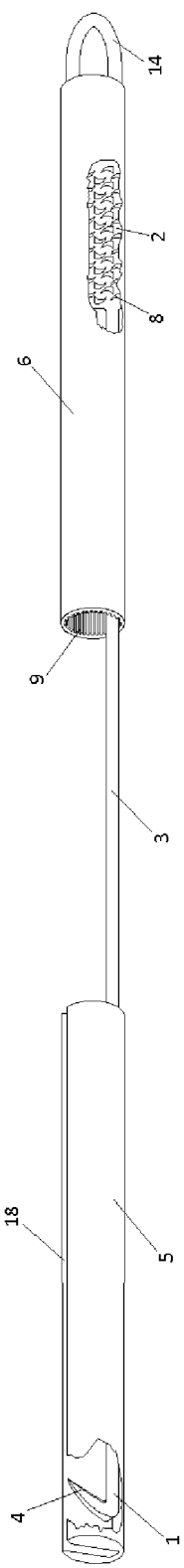
FIG. 1 shows the complete device, we can see the two anchor elements (1) and (2) on its ends. The sheaths (5) and (6) are also shown inside the device.
Figure 2:
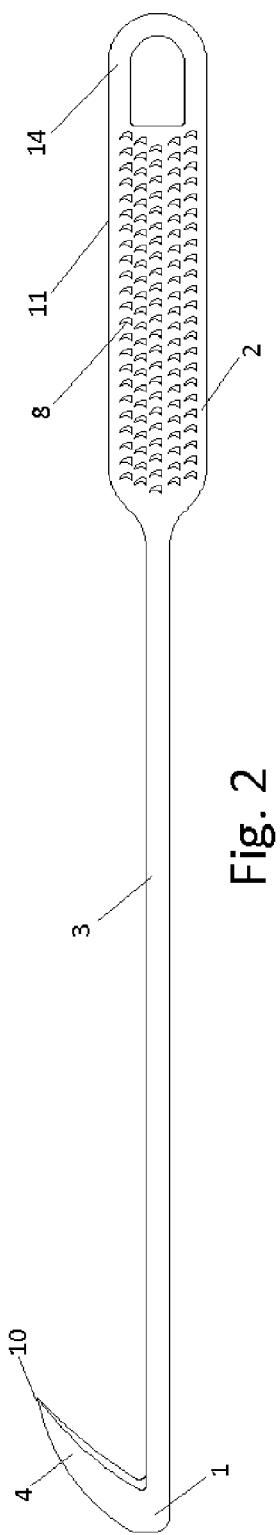
FIG. 2 shows the complete device, we can see the two anchor elements (1) and (2) on its ends and the flexible thread in the middle (3).
Figure 3:
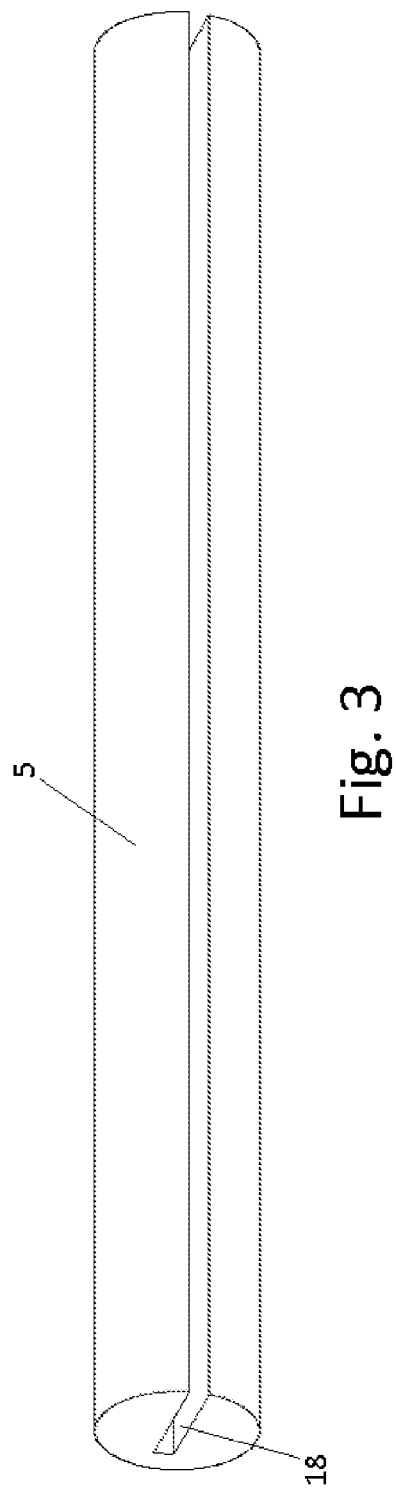
FIG. 3 shows the sheath (5) from a longitudinal view.
Figure 4:
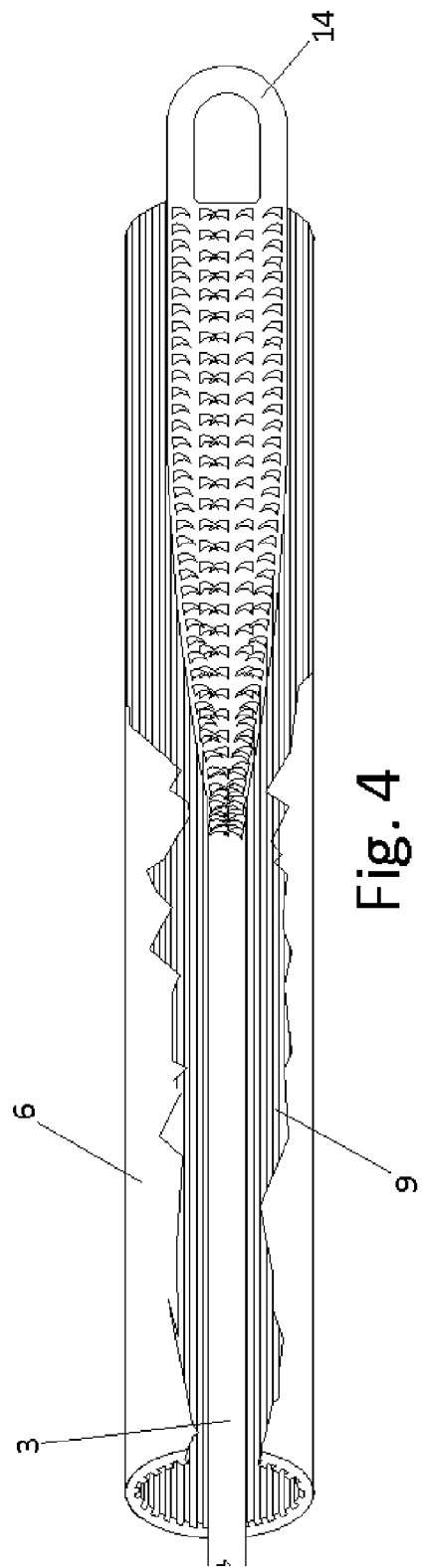
FIG. 4 shows the sheath (6) from a longitudinal view.
Figure 5:
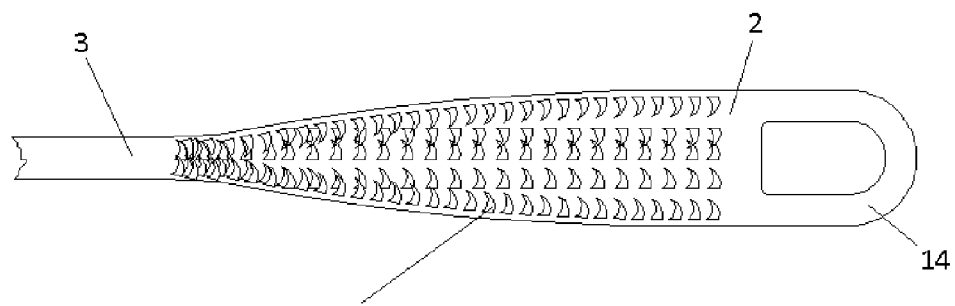
FIG. 5 shows a detailed view of the anchor element (2).
Figure 6:
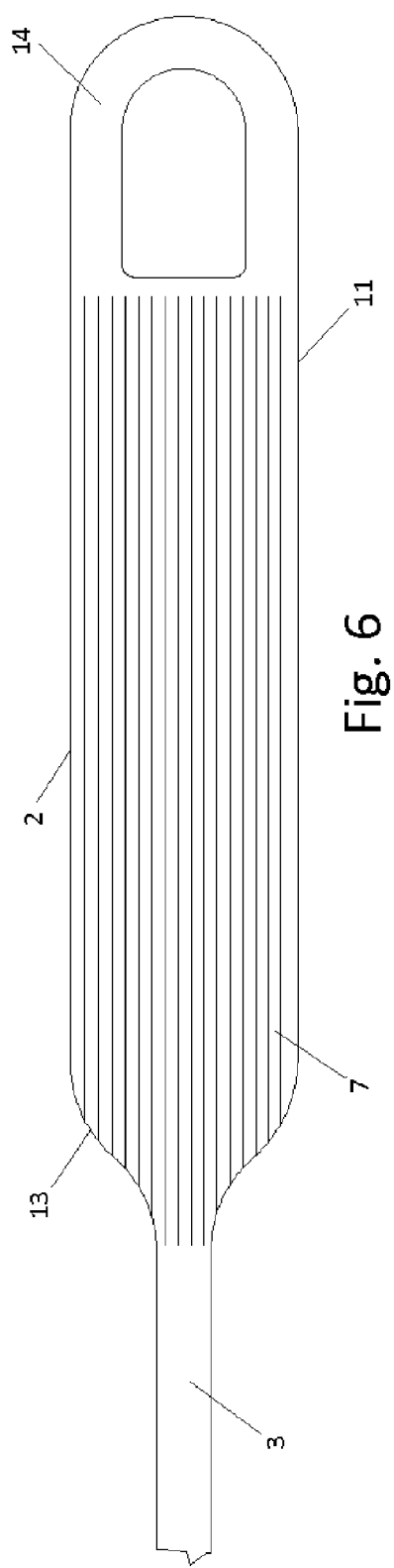
FIG. 6 shows a detailed view of the anchor element (2) on its opposite face.
Figure 7:
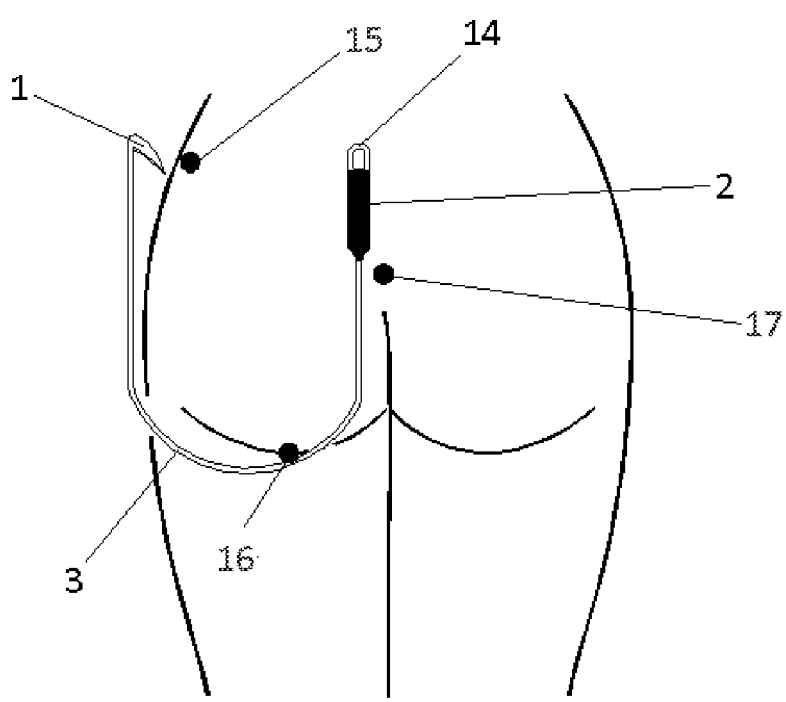
FIG. 7 portrays the human body and the incision points (15), (16), (17), and also the device in its working place.
Figure 8:
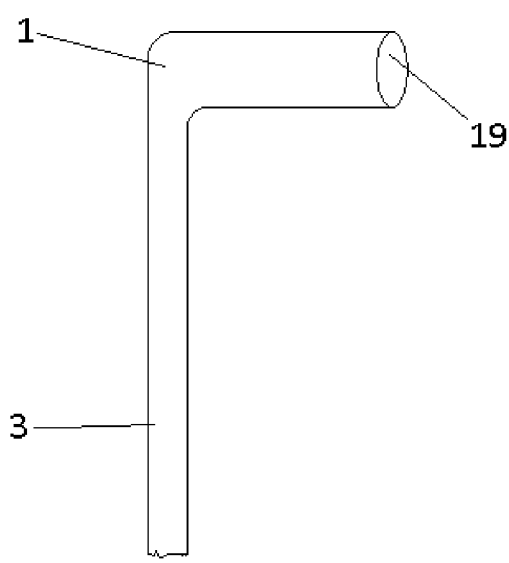
FIG. 8 shows a detailed view of the anchor element (1) in its cylindrical form (19).

According to this invention, the device has a longitudinal shape but is flexible, and is composed of three main elements. The first element is defined as the first anchor element (1), located on one of the ends of the device. This anchor element (1) is meant to be fixed on the anterior-superior iliac spine. Adjacent to this first anchor (1) along the longitudinal direction of the device we find the second main element, defined as the smooth resistant thread (3), which is completely smooth and is meant to take on and push the mass of the gluteus. The smooth thread (3) extends from a specific length and is joined to the third main element, defined as the second anchor element (2), located on the opposite end of the first anchor element (1). The second anchor element (2) is meant to be attached to the aponeurosis lumbosacral node.

The first anchor element (1) extends in the exterior has a fin-like shape (4). This fin (4) is defined geometrically by two arcs that intersect at a distal point (10), and this makes for the anchor end (1). This fin can optionally (4) take on the shape of a cylinder (19)

The second anchor (2) is composed of a plane body (11) that has a rectangular shape or any other geometric shape that may be required. Multiple anchor teeth (8) stand out from one of the faces of the plane body (11). On the opposite face, the plane body (11) contains multiple guide channels (7) along its length. The plane body (11) has two rounded corners in the shape of half arcs (13) and ends in an ear-like shape (14).

The device described in this invention, contains two separate sections of covers and sheaths (5) and (6).

The first sheath (5), is intended to cover the first anchor (1) and part of the smooth thread (3). This is an elongated cylindrical body, which is traversed in its interior and along all of its length, from one end to the other, by a slot (18) that has a rectangular cross-section and entirely smooth walls. In the radial direction (18) there is a longitudinal opening in this sheath (5).

The second sheath (6), is intended to house the second anchor in its interior and part of the smooth thread (3). The second sheath (6) is defined by an elongated cylindrical body, which is traversed longitudinally in its interior by a circular cavity from one end to the other. The interior walls of the sheath (6) posses channels, and these channels (9) coincide geometrically with the channels (7) that are located on the opposite face of the plane body (11) of the device.

The first and second anchor point are housed inside the first and second sheath respectively. The first anchor (1), can be easily slided into the slot since it has smooth walls and a trans-sectional area equal to the slot's geometry (18). In this manner the sheath (5) covers the anchor completely (1), specially its end (10). The anchor (1) can be manipulated easily at the moment when surgery is performed.

The second anchor element (2) must be rolled up into a cylinder shape, with its anchor teeth (8) facing the interior of the roll and the channels (7) facing the exterior, making an elongated cylinder with an exterior diameter that coincides with the diameter of the internal opening of the sheath (6) and can be slided into it, FIG. 1. The way we manage to have the anchor (2) bent inside the sheath (6), thus avoiding the sheath to be to big and the teeth (8) from adhering and entangling with it.

According to this invention and in this manner, the device to perform Glutopexia is complete and all of its element are in the right place.

Usage Instructions of the Invention

This invention is applied to a surgical method. We start by making incisions; the first one in the iliac region (15), and a second one at the level of the sub-gluteus furrow (16), and a third incision in the area in the intergluteus region at lumbosacral level (17).

The sheath in introduced in the incision (15) made at the level of the iliac crest, which contains the anchor element in its interior (1), leading the device towards the region in the subgluteus furrow. When the device appears at incision (16) made in the subgluteus furrow region, the fin (4) is attached to the crest of the iliac bone. A perforation is made on this bone similar to the negative shape of the fin (4). The sheath (5) has a slot (18), it allows for the removal of the sheath (5) from the device and the body of the patient, and making use of the incision made in the sub-gluteus region.

Then we introduce the second sheath (6) of the device, which carries the inside part of the smooth thread (3) and the anchor element (2), into incision (16) made in the sub-gluteus furrow, leading the device towards the inter-gluteus region at lumbosacral level.

When the device appears at incision (17) made in the inter-gluteus region, the sheath (6) is pulled and removed completely from the device. Once the sheath has been removed (6), the anchor element (2) which was inside it, will open up and uncover its anchor teeth (8).

Following this, the same procedure is made on the other gluteus and once both anchor elements (2) are in the intergluteus region, they are pulled uniformly using the ear-like shaped ends of the anchors (14) and they are attached to the ligament known as the lumbosacral aponeurosis.

The invention claimed is:

1. A device for gluteus lifting or "Gluteopexia", comprising a first anchoring element, a second anchoring element, the first anchoring element and the second anchoring element united by a longitudinal element, where the first anchoring element contains a fin in one end, which protrudes from the first anchoring element and having an edged end, and where the second anchoring element is composed of a flat body, where a face of the flat body has multiple protruding anchoring teeth and an opposite face on the flat body containing multiple longitudinal guide channels, the flat body having a rounded end, and where the longitudinal element has flat walls; the first anchoring element, the second anchoring element, and the longitudinal element are united composing a single body and the first anchoring element contains a first cover formed into a cylindrical elongated body and where the first cover contains a longitudinal crevice, and where the second anchoring element contains a second cover, which has in its interior walls a longitudinal hole with a circular section, and the interior walls of the second cover have channels, which are projected longitudinally.

2. The device for gluteus lifting or "Gluteopexia", according to claim 1, wherein the fin of the first anchoring element is geometrically defined by two arcs that intersect at a distal point, thus generating the edge of the the first anchoring element.

3. The device for gluteus lifting or "Gluteopexia", according to claim 1, wherein the flat body that composes the second anchoring element has a rectangular geometric shape, quadrangular, triangular or polygonal shape.

4. The device for gluteus lifting or "Gluteopexia", according to claim 3, wherein the flat body has tips rounded by means of a first arc and a second arc.

5. The device for gluteus lifting or "Gluteopexia", according to claim 1, wherein the multiple longitudinal guide channels of the second anchoring element coincide geometrically with the channels that are on the interior walls of the longitudinal hole with the circular section of the second cover.

6. The device for gluteus lifting or "Gluteopexia", according to claim 1, wherein the first anchoring element and the second anchoring element are lodged within the first cover and second cover respectively.

7. The device for gluteus lifting or "Gluteopexia", according to claim 6, wherein the first anchoring element, has a transversal area of geometric shape equal to geometry of the longitudinal crevice of the first cover.

8. The device for gluteus lifting or "Gluteopexia", according to claim 1, wherein the first cover covers the first anchoring element entirely.

9. The device for gluteus lifting of "Gluteopexia", according to claim 1, wherein the second anchoring element comprises an elongate cylinder.

10. The device for gluteus lifting or "Gluteopexia", according to claim 9 wherein a diameter of the second anchoring element matches an internal diameter of the second cover and wherein the second anchoring element may be slided into the second cover.

11. The device for gluteus lifting or "Gluteopexia", according to claim 1, wherein the fin in one end which protrudes from the first anchoring element has a shape of a blunted cylinder.

\* \* \* \* \*